US00PP17725P3

(12) United States Plant Patent

Nelson et al.

(10) Patent No.: US PP17,725 P3

(45) Date of Patent: May 15, 2007

(54) STRAWBERRY PLANT NAME 'BG-1975'

(50) Latin Name: *Fragaria ananassa*
Varietal Denomination: BG-1975

(75) Inventors: Steven D. Nelson, Watsonville, CA (US); Michael D. Nelson, Watsonville, CA (US); Lee W. Stoeckle, Ventura, CA (US)

(73) Assignee: Berry Genetics, Inc., Freedom, CA (US)

( * ) Notice: Subject to any disclaimer, the term of this patent is extended or adjusted under 35 U.S.C. 154(b) by 0 days.

(21) Appl. No.: 11/221,865

(22) Filed: Sep. 9, 2005

(65) Prior Publication Data

US 2007/0061929 P1 Mar. 15, 2007

(51) Int. Cl.
*A01H 5/00* (2006.01)

(52) U.S. Cl. ..... Plt./208

(58) Field of Classification Search ..... Plt./208
See application file for complete search history.

(56) References Cited

PUBLICATIONS

Mexican PBR Application No. 622 filed Oct. 10, 2005 (Copy of the Application as filed in Mexico) listing the Assigned Application Number and Variety Denomination (21 pgs.).

European Union Community Plant Variety Office (CPVO) Communication dated Nov. 30, 2006 for CPVO No. 2005/1829 as filed on Oct. 3, 2005 confirming the Assigned Application Number and Variety Denomination (2 pgs.).

*Primary Examiner*—Kent Bell
*Assistant Examiner*—Annette H Para
(74) *Attorney, Agent, or Firm*—Foley & Lardner LLP

(57) ABSTRACT

This invention relates to a new and distinct short-day variety of strawberry plant named 'BG-1975'. This new strawberry variety 'BG-1975' is primarily adapted to the growing conditions of the southern coast of California, and is primarily characterized by foliage medium to small in size and light to medium green in color, production is early, beginning as early as late December, producing upwards of 50% to 60% of it production by the end of March, produced fruit is attractive and of excellent quality, produced fruit is orange red to red in color, medium to large in size, very firm, conical to cylindrical in shape with a smooth surface lacking creases and ridges, and seeds may be slightly sunken below the surface.

4 Drawing Sheets

Latin name of the genus and species of the plant claimed: *Fragaria ananassa.*

Variety denomination: 'BG-1975'.

BACKGROUND OF THE INVENTION

The present invention relates to a new and distinct short-day strawberry variety designated as 'BG-1975'. This new variety is a result of a controlled cross made by the Inventors, Steven D. Nelson, Michael D. Nelson and Lee W. Stoeckle, in 1999 between strawberry variety designated 'BG-269' (patented, U.S. Plant Pat. No. 12,628) and strawberry variety designated 'BG-633' (patented, U.S. Plant Pat. No. 13,320). The variety is botanically known as *Fragaria ananassa.*

The seedling resulting from the aforementioned cross was asexually propagated by stolons in a nursery located in Siskiyou County, Calif., and was subsequently selected by the Inventors from a controlled breeding plot near Oxnard, Calif., in 2001. After its selection, the new variety was further asexually propagated by stolons in both Siskiyou County, Calif., and San Joaquin County, Calif.. The new variety was extensively tested over the next several years in fruiting fields near Oxnard, Calif. This propagation has demonstrated that the combination of traits disclosed herein, as characterizing the new variety, are fixed and remain true to type through successive generations of asexual reproduction.

BRIEF SUMMARY OF THE INVENTION

'BG-1975' is primarily adapted to the climate and growing conditions of the southern coast of California. This region provides the necessary winter temperatures required for it to produce a strong vigorous plant and to remain in fruit production from January through June. The nearby Pacific Ocean provides the needed humidity and moderate temperatures to maintain fruit quality during the winter and spring production months.

The following traits have been repeatedly observed and are determined to be unique characteristics of 'BG-1975', which in combination distinguish this strawberry plant as a new and distinct variety:

1. foliage medium to small in size and light to medium green in color;
2. production is early, beginning as early as late December, producing upwards of 50% to 60% of it production by the end of March;
3. produced fruit is attractive and of excellent quality;
4. produced fruit is orange red to red in color, medium to large in size, very firm, conical to cylindrical in shape with a smooth surface lacking creases; and
5. ridges, and seeds may be slightly sunken below the surface.

The strawberry varieties that are believed to be most closely related to the new strawberry variety 'BG-1975' are the parental strawberry variety 'BG-269' (patented, U.S. Plant Pat. No. 12,628) and the strawberry variety 'BG-625' (patented, U.S. Plant Pat. No. 13,255).

In comparison to the similar strawberry varieties 'BG-269' and 'BG-625', 'BG-1975' differs by the following combination of characteristics as described in Table 1:

TABLE 1

| Characteristic | 'BG-1975' | 'BG-269' (PP 12,628) | 'BG-625' (PP 13,255) |
|---|---|---|---|
| Plant | | | |
| Size | medium-large | large | medium-large |
| Crowns per Plant | few (1.8) | medium (2.8) | medium (2.8) |
| Foliage/Petioles | | | |
| Color | medium-light green | medium green | medium-light green |
| Leaf size | medium-small | medium-large | medium |
| Blistering | weak-medium | medium-strong | medium |
| Gloss | weak-medium | medium-strong | medium-strong |
| Frequency of bract leaflets | few (20–25%) | some (60–70%) | occasionally (35–40%) |
| Petiole pubescence | heavy | moderate | heavy |
| Stipule anthocyanins | weak | weak | medium |
| Fruit | | | |
| Size | medium-large | large-very large | large |
| L/W ratio | slightly longer than broad | as long as broad | as long as broad |
| Shape | conical-cylindrical | conical-rounded | conical |
| Band without achenes | absent or very narrow | absent or very narrow | narrow |
| Unevenness of surface | weak | medium | absent or very weak |
| Color | orange red to red | dark red | orange red to red |
| Glossiness | medium-strong | medium-strong | strong |
| Insertion of achenes | level to below the surface | level with surface | level to above the surface |
| Inflorescences | | | |
| Pubescence | strong | medium to weak | medium |
| Flower size | medium | large | large |
| Time of ripening | early | medium | medium |

For identification, a series of molecular markers have been determined for this new variety.

BRIEF DESCRIPTIONS OF THE DRAWINGS

The accompanying color photographs illustrate the overall appearance of typical specimens of the new strawberry variety 'BG-1975' at various stages of development as true as is reasonably possible with color reproductions of this type. Color in the photographs may differ slightly from the color value cited in the botanical description which accurately describe the color of 'BG-1975'. The depicted plant and plant parts of the new strawberry variety 'BG-1975' were taken in Oxnard, Calif., and are approximately 5 to 6 months old.

DETAILED BOTANICAL DESCRIPTION

Figure 1:
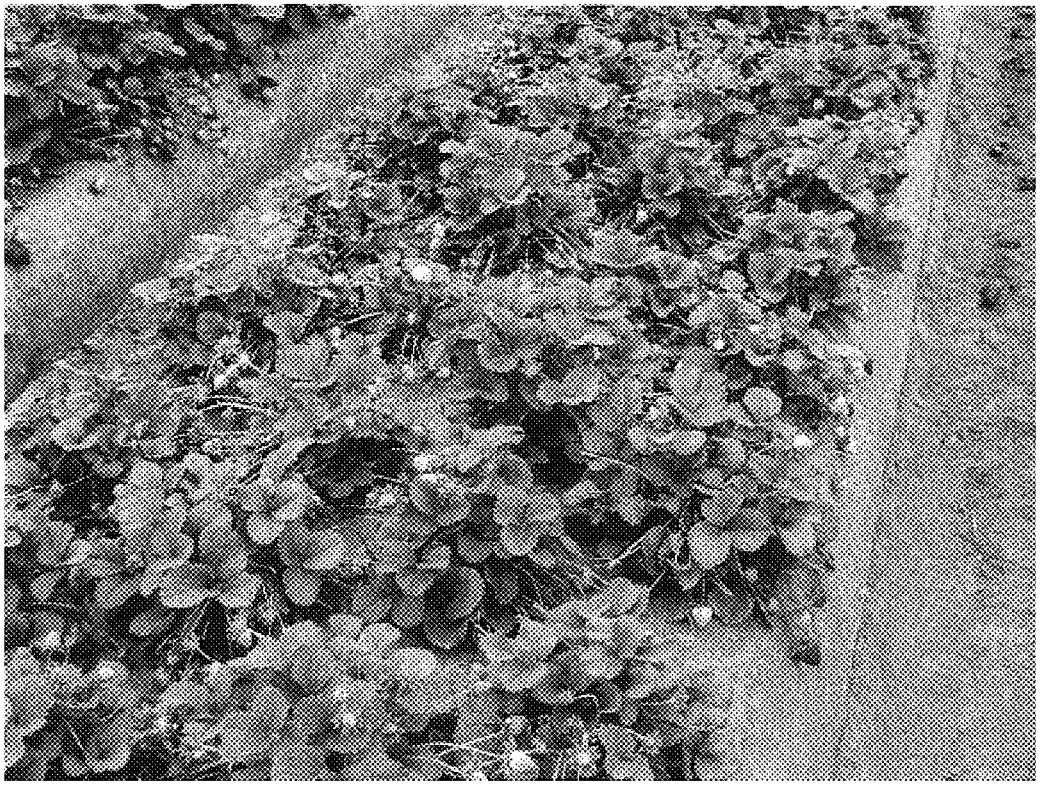
FIG. 1 shows typical fruiting field characteristics on Apr. 8, 2004.
Figure 2:
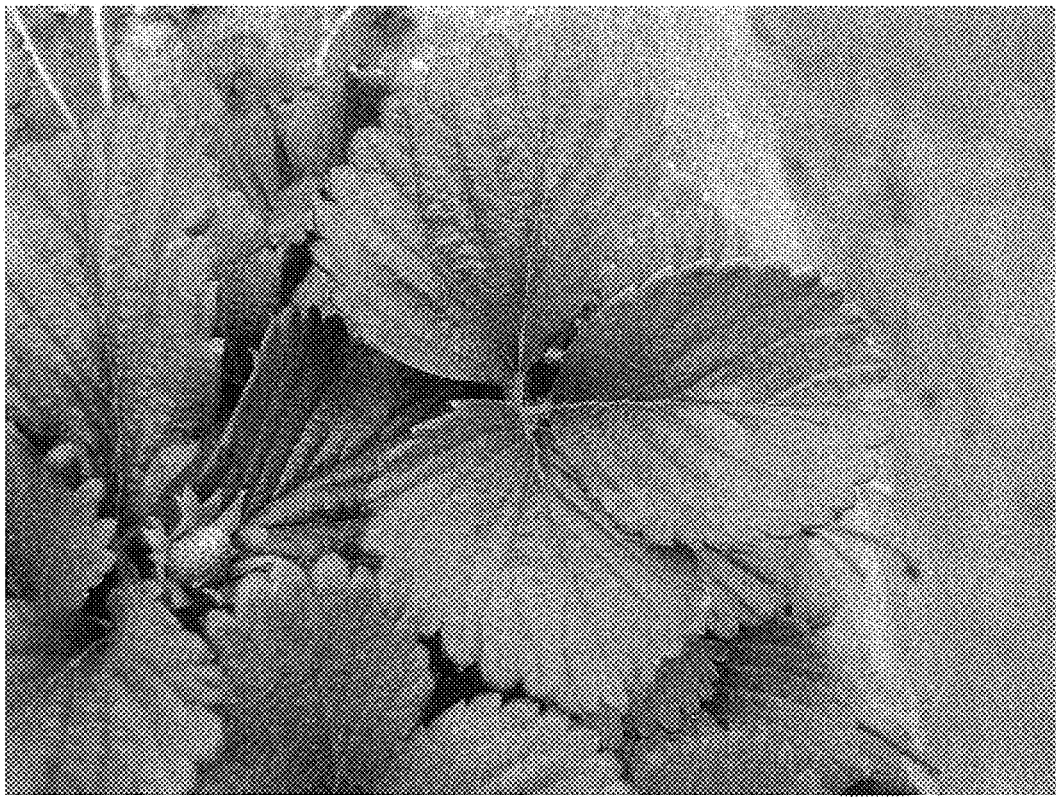
FIG. 2 shows a close-up view of a typical mature trifoliate on Apr. 8, 2004.
Figure 3:
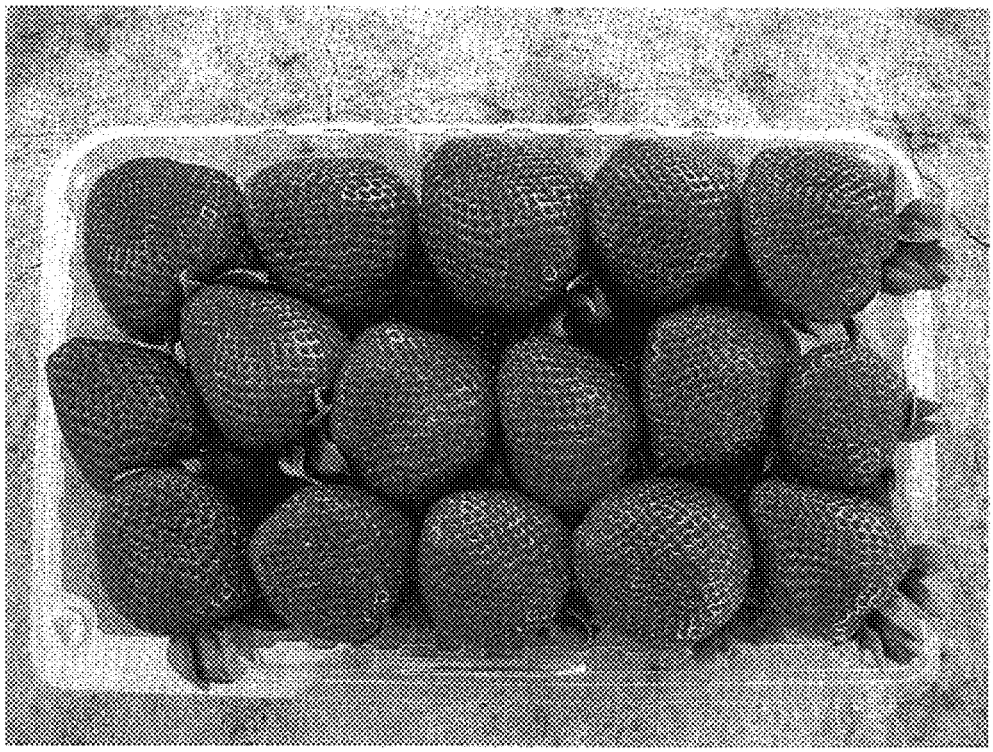
FIG. 3 shows a close-up view of fruit on Mar. 25, 2005.
Figure 4:
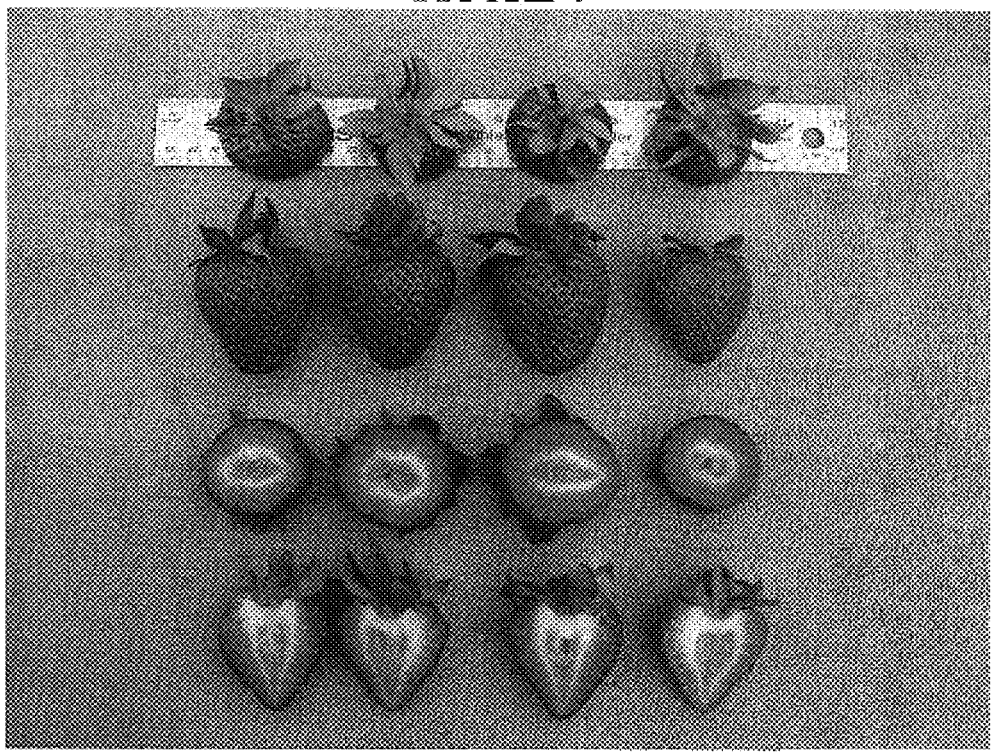
FIG. 4 shows typical internal and external fruit characteristics on Mar. 28, 2005.
Figure 5:
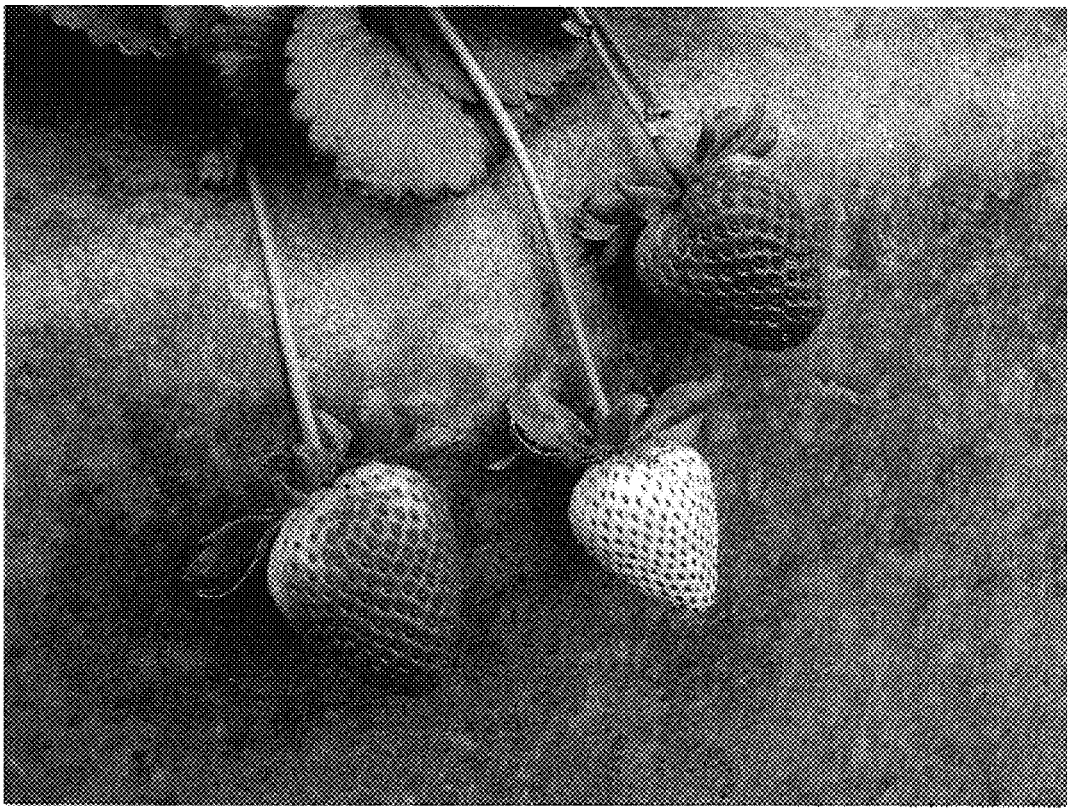
FIG. 5 shows typical mature and immature field fruit on Apr. 8, 2004.

'BG-1975' has not been observed under all possible environmental conditions. The characteristics of the new variety may vary in detail, depending upon variations in environmental factors, including weather (temperature, humidity and light intensity), day length, soil type and location.

The aforementioned photographs, together with the following description of the new strawberry variety 'BG-1975', unless otherwise noted, is based on observations taken during the 2005 growing season in Oxnard, Calif. These measurements and ratings were taken from plants of 'BG-1975' dug from a high-elevation nursery located in Siskiyou County, Calif., during the first week of October 2004 and planted 4 days later in Oxnard, Calif. The approximate age of the observed plants are 5 to 6 months. Yield observations and fruity quality characteristics are averaged from three years of data collected from the 2003 through the 2005 growing seasons.

Color terminology follows the Munsell Book of Colors, Munsell Color, Baltimore, Md. (1976).

Fruit characteristics: Tables 2, 3 and 4 describe the fruit, fruit production and fruit quality characteristics of 'BG-1975'. Fruit characteristics are taken from secondary fruit on a first year planting.

TABLE 2

2003–2005 market fruit yield and fruit size characteristics of 'BG-1975' with standards from Oxnard, California.

| Cultivar | 2003–2005 Average Fresh Yield GM/PL | 2003–2005 Average Freezer Yield GM/PL | 2003–2005 Average Fruit Size GRM |
|---|---|---|---|
| 'BG-1975' | 806 | 157 | 28.6 |
| 'BG-269' | 940 | 244 | 29.6 |
| 'BG-625' | 782 | 177 | 28.8 |

Fruit was harvested from January through June 2003–2005. The plants of 'BG-1975' were dug from a high elevation nursery (Macdoel, California) during the first week of October and planted approximately 3 to 4 days later in Oxnard, California. 'BG-1975' is compared with standards dug and planted comparably.

TABLE 3

Comparison of 2003–2005 fruit quality characteristics, including flavor and soluble solids of 'BG-1975', with standards from Oxnard, California.

| Character | 'BG-1975' | 'BG-269' | 'BG-625' |
|---|---|---|---|
| Skin Firmness* | 8.2 | 8.0 | 8.5 |
| Fruit Appearance* | 8.0 | 7.6 | 8.0 |
| Fruit Gloss* | 8.0 | 8.0 | 8.8 |
| Flavor** | 2.8 | 2.6 | 2.8 |
| Soluble Solids*** | 7.5 | 8.1 | 7.4 |

*Results are averaged from 3 years of data collected from January through May 2003–2005. Ratings are based on a scale from 1–10; the higher the rating, the stronger the skin and more attractive and glossy the berry.
**Results are averaged from 2 years of data collected from March through May 2004–2005. Ratings are based on a scale from 1–5; the higher the rating the better the flavor.
***Results are averaged from 2 years of data collected from March through May 2004–2005. Soluble solid content is measured in percent Brix, with percent Brix being an indirect measurement of the sugar content in the fruit.

TABLE 4

Comparison of secondary fruit characteristics of 'BG-1975', with standards from Oxnard, California, Mar. 25, 2005.

| Character | 'BG-1975' | 'BG-269' | 'BG-625' |
|---|---|---|---|
| Munsell Color Range Mature Fruit | 7.5 R 3/10 to 3/12 | 7.5 R 2/8 to 3/8 | 7.5 R 3/12 to 4/12 |
| Fruit Length mean (cm) | 4.6 | 4.5 | 4.4 |

TABLE 4-continued

Comparison of secondary fruit characteristics of 'BG-1975', with standards from Oxnard, California, Mar. 25, 2005.

| Character | 'BG-1975' | 'BG-269' | 'BG-625' |
|---|---|---|---|
| Fruit Width mean (cm) | 4.2 | 4.3 | 4.1 |
| Fruit Length/ Width Ratio | 1.10 | 1.00 | 1.10 |
| Calyx Diameter mean (cm) | 5.4 | 5.8 | 5.4 |
| No. Sepals/Berry | 14.4 | 14.8 | 11.9 |

Fruit:

*Ratio of length/width.*—As long as broad to slightly longer than broad.
*Size.*—Medium to large.
*Predominant shape.*—Conical to almost cylindrical.
*Difference in shapes between primary and secondary fruit.*—Slight to moderate.
*Band without achenes.*—Absent or very narrow.
*Unevenness of surface.*—Weak.
*Color of mature fruit.*—Orange red to red (7.5R 3/10 to 3/12).
*Evenness of color.*—Slightly uneven to even.
*Glossiness.*—Medium to strong.
*Insertion of achenes.*—Below surface to level with surface.
*Insertion of calyx.*—In basin.
*Attitude of the calyx segments.*—Spreading.
*Size of calyx in relation to fruit diameter.*—Slightly larger to much larger.
*Adherence of calyx* (*when fully ripe*).—Very strong.
*Firmness of skin.*—Medium to strong.
*Firmness of flesh.*—Medium.
*Color of flesh.*—Medium red (7.5 R 4/12 to 4/14).
*Distribution of red color of the flesh.*—Marginal and central.
*Hollow center.*—Moderately expressed.
*Receptacle color.*—Whitish (N 9.25/84.2%R to 9/78.7%R).
*Seed color.*—Moderate yellow to dark red (5 Y 6/8 to 7.5 R2/8).
*Seed size.*—Medium (average 0.67 mgs).
*Time of flowering* (*50% of plants at first flower*).—Early.
*Time of ripening* (*50% of plants with ripe fruit*).—Early.
*Type of bearing.*—Not remontant.

Plant characteristics: Table 5 describes plant characteristics of 'BG-1975'. Plant characteristics are taken from a fully mature mid season plant.

TABLE 5

Comparison of plant characteristics of 'BG-1975', with standards from Oxnard, California, Mar. 25, 2005.

| Character | 'BG-1975' | 'BG-269' | 'BG-625' |
|---|---|---|---|
| Plant Height mean (cm) | 15.7 | 15.2 | 17.4 |
| Plant Spread mean (cm) | 28.1 | 28.3 | 28.6 |
| Crowns/Plant (mean) | 1.8 | 2.8 | 2.8 |

Plant:

*Size.*—Medium to large.
*Habit.*—Globose.
*Density.*—Medium.
*Vigor.*—Medium to strong.
*Stolons.*—Number: Medium. Anthocyanin coloration: Weak (7.5 R 5/6 to 6/6). Thickness: Medium. Pubescence: Strong.

Foliage characteristics: Table 6 describes foliage characteristics of 'BG-1975'. Foliage characteristics are taken from a fully mature tri-foliate during mid season.

TABLE 6

Comparison of leaf characteristics of 'BG-1975', with standards from Oxnard, California, Mar. 25, 2005.

| Character | 'BG-1975' | 'BG-269' | 'BG-625' |
|---|---|---|---|
| Munsell Color Range (upper surface) | 5 GY 4/4 to 3/6 | 7.5 GY 3/4 to 3/6 | 7.5 GY 3/4 to 3/6 |
| Terminal Leaflet Length mean (cm) | 6.4 | 7.6 | 7.6 |
| Terminal Leaflet Width mean (cm) | 6.0 | 6.3 | 6.9 |
| Terminal Leaflet ratio (L/W) | 1.06 | 1.19 | 1.10 |
| Petiole Length mean (cm) | 11.2 | 11.8 | 12.9 |
| Petiole Width mean (mm) | 3.0 | 3.0 | 4.0 |
| Petiolule Length mean (mm) | 5.7 | 7.0 | 6.0 |
| Serrations/Leaf | 20.8 | 19.8 | 20.1 |
| Stipule Length mean (cm) | 1.4 | 1.6 | 1.9 |
| Stipule Width mean (cm) | 1.3 | 1.0 | 1.2 |

Foliage:

*Color of upper surface.*—Light to medium green (5 GY 4/4 to 3/6).
*Color of under side.*—Medium grey green (7.5 GY 5/4 to 6/4).
*Shape in cross section.*—Slightly concave to flat.
*Blistering.*—Weak to medium.
*Glossiness.*—Weak to medium.
*Number of leaflets/leaf.*—Three.
*Terminal leaflet.*—Size: Medium to small. Length/width ratio: As long as broad to slightly longer than broad. Shape of base: Acute. Shape of incision of margins: Rounded.
*Petiole.*—Pubescence: Heavy.
*Stipule color.*—Medium green (2.5 GY 6/6 to 6/8).
*Anthocyanin coloration of stipule.*—Weak.
*Attitude of hairs.*—Strong outward.
*Frequency of bract leaflets.*—Few (occur on approx. 20–25% of petioles).

Flowers and inflorescences: Table 7 describes inflorescence and flower characteristics of 'BG-1975'. Inflorescence characteristics are taken from a fully mature plant while flower characteristics are taken from a secondary flower during mid season.

TABLE 7

Comparison of inflorescence and secondary flower characteristics of 'BG-1975', with standards from Oxnard, California, Mar. 25, 2005.

| Character | 'BG-1975' | 'BG-269' | 'BG-625' |
|---|---|---|---|
| Fruiting Truss Length* mean (cm) | 24.8 | 24.9 | 24.5 |
| Corolla Diameter mean (cm) | 2.5 | 3.0 | 2.8 |

TABLE 7-continued

Comparison of inflorescence and secondary flower characteristics of 'BG-1975', with standards from Oxnard, California, Mar. 25, 2005.

| Character | 'BG-1975' | 'BG-269' | 'BG-625' |
|---|---|---|---|
| Calyx Diameter mean (cm) | 3.3 | 4.0 | 3.8 |
| Petal Length mean (cm) | 1.1 | 1.2 | 1.1 |
| Petal Width mean (cm) | 1.0 | 1.3 | 1.2 |
| Petal L/W Ratio | 1.03 | 0.93 | 0.94 |
| Petals/Flower (mean) | 6.3 | 6.5 | 5.7 |
| Sepal Length mean (cm) | 1.3 | 1.5 | 1.5 |
| Sepal Width mean (cm) | 0.5 | 0.6 | 0.6 |
| Sepal L/W Ratio | 2.58 | 2.51 | 2.51 |
| Sepals/Flower (mean) | 12.9 | 13.0 | 11.3 |

*As measured from the base of the primary peduncle where it attaches to the crown of the plant to the furthest berry.

Inflorescence:

*Position relative to foliage.*—Level with to above.

*Pubescence.*—Strong.

*Anthocyanins.*—Very light to none.

*Fruiting truss length.*—24.8 cm.

Flowers:

*Color.*—White (N 9.5/90.0%/R to N 9.25/84.2% R).

*Size.*—Medium.

*Size of calyx relative to corolla.*—Larger.

*Relative position of petals.*—Overlapping.

*Petal length/width ratio.*—As long as broad to longer than broad.

Pest reactions: This new variety may not be resistant to any of the known insects, diseases or viruses common in California. It is known to be tolerant to the two-spotted spider mite, aphid and flower thrips when treated properly. It is also known to be moderately tolerant to grey fruit mold, powdery mildew and angular leaf spot. The susceptibility of the new variety to any of the virus complexes of California has not been determined.

We claim:

1. A new and distinct strawberry plant named 'BG-1975', as herein described and illustrated by the characteristics set forth above.

* * * * *